(12) United States Patent
Schute et al.

(10) Patent No.: US 8,487,987 B2
(45) Date of Patent: Jul. 16, 2013

(54) CAMERA ADAPTOR FOR A MEDICAL-OPTICAL OBSERVATION INSTRUMENT AND CAMERA-ADAPTOR COMBINATION

(75) Inventors: Stefan Schute, Aalen (DE); Artur Hoegele, Oberkochen (DE)

(73) Assignee: Carl Zeiss Meditec AG (DE)

( * ) Notice: Subject to any disclaimer, the term of this patent is extended or adjusted under 35 U.S.C. 154(b) by 516 days.

(21) Appl. No.: 12/712,492

(22) Filed: Feb. 25, 2010

(65) Prior Publication Data

US 2010/0214402 A1 Aug. 26, 2010

(30) Foreign Application Priority Data

Feb. 26, 2009 (DE) .................. 10 2009 010 448

(51) Int. Cl.
*H04N 7/18* (2006.01)
(52) U.S. Cl.
USPC ............. 348/77; 348/68; 348/75; 348/223.1; 345/473; 359/690; 396/529; 386/227; 600/167
(58) Field of Classification Search
None
See application file for complete search history.

(56) References Cited

U.S. PATENT DOCUMENTS

| | | | | |
|---|---|---|---|---|
| 3,704,658 A * | 12/1972 | Uesugi | ............. | 396/529 |
| 4,143,938 A | 3/1979 | Feinbloom | | |
| 5,245,475 A * | 9/1993 | Takasugi | ......... | 359/690 |
| 5,264,928 A | 11/1993 | Howes | | |
| 5,835,266 A | 11/1998 | Kitajima | | |
| 6,069,651 A * | 5/2000 | Tsuyuki et al. | .......... | 348/75 |
| 6,277,067 B1 * | 8/2001 | Blair | ............. | 600/167 |
| 2001/0048549 A1 | 12/2001 | Wang | | |
| 2002/0012045 A1 | 1/2002 | Nomura et al. | | |
| 2003/0035048 A1 * | 2/2003 | Shipp | ............. | 348/68 |
| 2005/0111088 A1 | 5/2005 | Winterot et al. | | |
| 2007/0018989 A1 * | 1/2007 | Roberts et al. | ......... | 345/473 |
| 2007/0269188 A1 * | 11/2007 | Shiga | ............. | 386/107 |
| 2008/0152337 A1 | 6/2008 | Gartner et al. | | |
| 2008/0246856 A1 * | 10/2008 | Shibuya et al. | ......... | 348/223.1 |

FOREIGN PATENT DOCUMENTS

| | | |
|---|---|---|
| DE | 93 08 464.1 | 9/1993 |
| DE | 295 14 244 | 3/1996 |
| DE | 199 38 466 | 2/2000 |
| DE | 200 10 121 | 2/2001 |
| DE | 103 55 527 | 6/2005 |
| JP | 2002-6195 | 1/2002 |
| WO | 01/79910 | 10/2001 |

* cited by examiner

*Primary Examiner* — Sath V Perungavoor
*Assistant Examiner* — Dakshesh Parikh
(74) *Attorney, Agent, or Firm* — Gerald E. Hespos; Michael J. Porco; Matthew T. Hespos

(57) ABSTRACT

A camera adaptor (19) is provided for connecting a camera (21) to an interface (13) of a medical-optical observation instrument (1) with a parallel beam path. The interface (13) is situated in the parallel beam path (9a, 9b) of the medical-optical observation instrument (1). The camera adaptor (19) has an instrument connector part (41) for connection to the interface (13) of the medical-optical observation instrument (1) and a camera connector part (43, 143) for connection to a camera (21). The beam path (43) runs through the camera adaptor (19) along a linear optical axis. The camera adaptor (19) has an objective-lenses combination (47) with a total focal length between 40 mm and 120 mm. A lens with a positive partial focal length leading on the instrument side in the objective-lenses combination (47) and is followed, on the side toward the camera, by a lens with a negative partial focal length.

32 Claims, 9 Drawing Sheets

CAMERA ADAPTOR FOR A MEDICAL-OPTICAL OBSERVATION INSTRUMENT AND CAMERA-ADAPTOR COMBINATION

BACKGROUND OF THE INVENTION

1. Field of the Invention

The present invention relates to a camera adaptor for a medical-optical observation instrument, in particular for a surgical microscope. In addition, the present invention relates to a combination of a camera adaptor and a camera.

2. Description of the Related Art

So-called phototubes are often available in research microscopes for photographic or video-technical recording of an observation object. In the case of a stereoscopic microscope, there then is, for example, a third connecting piece to which a camera housing without a camera objective is generally connected, in addition to the two eyepiece connecting pieces. However, DE 200 10 121 U1 has also disclosed camera adaptors, which have an attachment apparatus for a camera and allow the use of a camera with an objective on the photo connecting piece. If there is no phototube on the microscope, it is possible to use a camera adaptor as described in US 2001/0048549 A1 for connecting a camera to an eyepiece connecting piece of an eyepiece tube.

The two aforementioned variants for connecting a photo camera or video camera to a microscope are however generally not suitable for connecting a camera to a surgical microscope. This is because a medical practitioner using the surgical microscope should be impeded as little as possible by a camera. Furthermore, in a surgical microscope, it is not always straightforwardly possible to arrange a decoupling apparatus for the phototube in the binocular beam path of the observer. By way of example, microsurgery often uses moveable tubes, so-called swivel tubes, to be able to ergonomically adapt a surgical microscope to the surgical situation. The use of a decoupling device in the binocular tube is not possible in swivel tubes.

The use of a camera at an eyepiece connecting piece of the stereo tube of the surgical microscope is excluded from the outset because the medical practitioner requires both eyepiece stages during an operation and thus no such eyepiece connecting piece is available for attaching a camera. Therefore, in surgical microscopes, the decoupling device with a camera connecting piece is situated in the region of the parallel beam path between the magnification changer and the binocular tube. Adaptors provided with an additional optical system, which allows the object observed by the microscope to be imaged on the camera chip, are then attached to such an output. Such an output for connecting a camera and corresponding adaptors are described in, for example, U.S. Pat. No. 5,835,266 and U.S. Pat. No. 5,264,928. Adaptors for use at such camera outputs of a surgical microscope are moreover described in US 2008/0152337 A1 and WO 01/799 10 A1. The described adaptors have angled optical systems with a mirror or a prism within the adaptor optical system, with the aid of which the image is displayed the right way up and the right way round on the image sensor of the camera. The display being the right way up and the right way round is important, particularly in the case of video recordings shown to an assistant or other auxiliary staff during the operation, because the display being the right way up and the right way round is of essential importance to the surgical staff.

Although the camera adaptor as per U.S. Pat. No. 5,264, 928 also comprises a non-angled beam path, the latter is only provided for connecting a photo camera. Images of a photo camera, which are without current importance to the treating medical practitioner or the auxiliary staff during the operation, do not however require an illustration of the operation site that is the right way up and the right way round. By contrast, the video camera in U.S. Pat. No. 5,264,928 is also attached to the camera adaptor via an angled beam path.

The camera adaptors with angled optical systems have a large installation volume and many optical elements. Moreover, the assembly and adjustment thereof is complicated and it is extremely difficult to attain a sufficiently high image quality in the adaptor optical system.

It is therefore an object of the present invention to provide a camera adaptor for a medical-optical observation instrument, which is particularly suitable for connecting a video camera, has a small installation volume and can be implemented with a sufficiently high image quality of the adaptor arrangement. A further object of the present invention is to provide an advantageous camera-adaptor combination for a medical observation instrument.

SUMMARY OF THE INVENTION

A camera adaptor according to the invention for connecting a camera to an interface of a medical-optical observation instrument, which comprises a parallel beam path and in which the interface is situated in the parallel beam path, comprises a instrument connector part for the connection to the interface of the medical-optical observation instrument and a camera connector part for the connection to a camera. Herein, the camera connector part can have, in particular, a bayonet cap or a so-called C-mount connector. In the camera adaptor according to the invention, the beam path runs along a linear optical axis, i.e. there are no mirrors or prisms for deflecting the beam path. The camera adaptor according to the invention furthermore has an objective-lenses combination with a focal length in the region of between 45 mm and 120 mm, in which there is, leading on the instrument side in the objective-lenses combination, a lens or lens combinations with a positive partial focal length, which is followed, on the side toward the camera, by a lens or lens combinations with a negative partial focal length. Herein, the medical-optical observation instrument can be e.g. an endoscope or a surgical microscope.

The objective-lenses combination and the linear optical axis, i.e. the dispensation of an angled optical axis, utilized in the camera adaptor according to the invention afford a reduced installation length of the camera adaptor according to the invention compared to camera adaptors from the prior art. Here, the invention is based, inter alia, on the recognition that the current conventional use of electronic image sensors, for example CCD sensors or CMOS sensors, makes electronic image erection possible in order to obtain a display of the observation object that is the right way up and the right way round, and that therefore deflecting optical elements such as mirrors or prisms can be dispensed with in the adaptor.

The described objective-lenses combination and the linear optical axis make it possible to obtain optical paths of <72 mm, in particular <66 mm and more particularly <60 mm between the optical axis of the beam path in the medical-optical observation instrument, to which the camera adaptor is coupled, and the reference plane of the camera connector part. If the camera connector part is designed as a C-mount connector, this reference plane is the C-mount reference plane of the camera head. As a result of the reduced dimensions of the optical path, the operating medical practitioner reliably remains unimpeded by the camera adaptor, particularly in the case of surgical microscopes.

In a first refinement of the camera adaptor according to the invention, the objective-lenses combination comprises a leading lens or lens combination on the instrument side with a positive partial focal length and a final lens or lens combination on the camera side with a negative partial focal length. Herein, in a particular variant of this refinement, the leading lens or lens combination on the instrument side can be a lens combination of three lenses, which together have a positive partial focal length. The objective-lenses combination comprises a single lens with a negative partial focal length as a final lens or lens combination on the camera side. Using such a lens combination, which can be characterized as a tele-system, aberrations, in particular chromatic aberrations, image sharpness aberrations and image scale aberrations, can be compensated for very well by using few lenses, in particular by using a total of only four lenses. If at least two lenses of the instrument-side lens combination are cemented together to form a cemented component, an achromatic design of the objective-lenses system with few reflections can additionally be implemented. With the use of only four lenses, this affords an image quality that has an RMS deviation of the wavefront of an average wavefront in the observation light of <0.08 lambda at a wavelength of lambda=515.7 nanometers. This corresponds to a Strehl ratio >0.80. In particular, such a lens combination can achieve an RMS deviation of <0.05 lambda (Strehl ratio>0.90) and even an RMS deviation of <0.03 lambda (Strehl ratio>0.95).

In particular, the objective-lenses combination with a leading lens combination on the instrument side made of three lenses on the instrument side, two of which are cemented together, and a final lens on the camera side can be designed such that the lens surfaces of the leading lens combination on the instrument side have, as seen from the instrument side to the camera side, a positive or negative radius of curvature, a negative radius of curvature, a negative or positive radius of curvature, a positive radius of curvature and a positive or negative radius of curvature. The lens surfaces of the final lens on the camera side then have, as seen from the instrument side to the camera side, a positive radius of curvature and a positive radius of curvature.

In the camera adaptor according to the first refinement, the total focal length of the objective-lenses combination can lie in the region of between 40 mm and 120 mm and in particular in the region of between 45 and 75 mm. By way of example, the total focal length can lie in the region of between 40 mm and 80 mm, in particular between 45 mm and 55 mm, or in the region of between 55 mm and 120 mm, in particular in the region of between 55 mm and 75 mm. The absolute value of the partial focal length of the final lens or lens combination on the camera side can be less than 110 mm; in particular, it can be less than 95 mm, less than 85 mm, less than 80 mm, less than 70 mm or less than 62 mm.

In a first specification of the first refinement, the camera adaptor according to the invention is designed such that it is suitable, in particular, for using a camera with a ⅓-inch image sensor (with a sensor diagonal of 6 mm). In this particular camera adaptor, the total focal length of the objective-lenses combination lies in the region of between 40 mm and 80 mm, in particular in the region of between 45 mm and 55 mm. Then, the absolute value of the partial focal length of the final lens or lens combination on the camera side is <80 mm, in particular <70 mm and more particularly <62 mm. In this refinement, a distance of <72 mm can be obtained between the optical axis of the beam path in the medical-optical observation instrument, to which the camera adaptor is coupled, and the camera connector part.

In a second specification of the first refinement, the camera adaptor according to the invention is suitable, in particular, for use with a camera that has a ½-inch image sensor (with a sensor diagonal of 8 mm). In this particular camera adaptor, the total focal length of the objective-lenses combination lies in the region of between 55 mm and 120 mm, in particular in the region of between 55 mm and 75 mm, and the absolute value of the partial focal length of the final lens or lens combination on the camera side is <110 mm, in particular <95 mm and more particularly <85 mm. In this refinement, a distance of <72 mm, in particular <66 mm and more particularly <60 mm, can also be obtained between the optical axis of the beam path in the medical-optical observation instrument, to which the camera adaptor is coupled, and the camera connector part.

In the first refinement of the camera adaptor according to the invention, the final lens or lens combination on the camera side can be arranged at a large distance from the leading lens combination on the instrument side, in particular at a distance corresponding to at least one lens thickness of the final lens on the camera side. Alternatively, the final lens or lens combination on the camera side can be arranged at a small distance from the leading lens combination on the instrument side, in particular at a distance of less than one lens thickness of the final lens on the camera side (in the following text, this is referred to as a "compact tele-system"). Here, the distance can also be zero and so the final lens or lens combination on the camera side butts against the leading lens combination on the instrument side.

In a second refinement of the camera adaptor according to the invention, in the objective-lenses combination, the lens or lens combinations with the negative partial focal length is/are followed, on the side of the camera, by a lens or lens combination with a positive partial focal length. Using such an objective-lenses combination, whose partial-focal-length combination is positive-negative-positive and which can be characterized as a triplet, aberrations, in particular chromatic aberrations, image sharpness aberrations and image scale aberrations, can also be compensated for very well by using few lenses. Herein, the lens or lens combinations with the negative partial focal length can be designed as a cemented component comprising two lenses in particular, as a result of which an achromatic design of the objective-lenses system with few reflections can be implemented. Furthermore, the leading lens or lens combination on the instrument side and the lens or lens combination following the cemented component can be designed as single lenses and so the objective-lenses combination of the second refinement can also be implemented using four lenses.

In a specification of the second refinement, the lens surfaces of the leading single lens on the instrument side can have, as seen from the instrument side to the camera side, a positive or negative radius of curvature and a positive or negative radius of curvature, the surfaces of the central lens combination can have, as seen from the instrument side to the camera side, a positive radius of curvature, a negative radius of curvature and a positive radius of curvature and the lens surfaces of the final single lens on the camera side can have, as seen from the instrument side to the camera side, a positive radius of curvature and a positive or negative radius of curvature.

In the camera adaptor according to the invention, the objective-lenses combination can thus be designed such that it only has four lenses in total, whether in the form of a tele-system or in the form of a triplet. Such a camera adaptor affords good imaging quality and a compact design at moderate production costs.

Thus, the installation length of the adaptor overall can be kept low, in particular so low that the entire optical system can be inserted into the interior of the connecting piece of the decoupling device of the medical-optical observation instrument and so no space is required in addition to the spatial requirements of the connecting piece.

Advantageously, the diameter of the entrance pupil of the camera adaptor is less than 18 mm and, in particular, lies in the region of between 6 mm and 16 mm. In particular, in respect of increasing the depth of focus, it can be advantageous to reduce the diameter of the entrance pupil to a value below 12 mm, for example to a value of between 6 mm and 12 mm. In this case, the entrance pupil is situated outside of the camera adaptor itself and, in the case of a camera adaptor coupled to the interface of a medical-optical observation instrument, it is situated deep within the interior of the medical-optical observation instrument, namely between the beam splitter of the decoupling apparatus and the objective lens of the observation instrument.

In order to allow an adjustment of the image position on the image sensor, the camera adaptor can comprise an adjustment device, with the aid of which a relative movement between a mounted camera and the objective-lenses combination perpendicular to the optical axis can be brought about, particularly in two dimensions.

Additionally or alternatively, the camera adaptor can comprise an adjustment device, with the aid of which a relative movement between a mounted camera and the objective-lenses combination along the optical axis can be brought about, in order to allow focusing of the image on the image sensor.

For further adjustment of the image position, the camera adaptor, additionally or alternatively, can have a tilting mechanism, with the aid of which a relative tilt between a mounted camera and the objective-lenses combination can be brought about.

Finally, there can be a variable stop in front of the objective-lenses combination on the instrument side, by means of which the illumination of the image sensor and the depth of focus of the image can be set. Moreover, it can be expedient to define or delimit the entrance pupil for the camera adaptor directly in front of the adaptor or at a small distance in front of the adaptor.

According to a further aspect of the invention, provision is made for a camera adaptor for connecting a camera to an interface of a medical-optical observation instrument comprising a parallel beam path, in which the interface is situated in the parallel beam path of the medical-optical observation instrument. The camera adaptor has an instrument connector part for the connection to the interface of the medical-optical observation instrument and a camera connector part for the connection to a camera, with the beam path running through the camera adaptor along a linear optical axis between the instrument connector part and the camera connector part. The camera adaptor comprises an objective-lenses combination with a total focal length in the region of between 40 mm and 120 mm, in which the objective-lenses combination comprises at least three and at most four lenses and there is, leading on the instrument side, a lens or lens combination with a positive partial focal length, which is followed, on the side toward the camera, by a lens or lens combination with a negative partial focal length.

The number of lenses should in this case not be understood strictly as the subject matter but should be understood functionally because the function carried out by a single lens in the objective-lenses combination can, in principle, also be implemented if this single lens is replaced by a lens combination having a plurality of lenses, which together lead to optical properties corresponding to those of the single lens.

A camera-adaptor combination according to the invention for a medical-optical observation instrument, for example for an endoscope or a surgical microscope, has a camera adaptor according to the invention and an electronic camera, which can be a photo camera and, in particular, a video camera and which is arranged on the camera connector part. The electronic camera comprises a unit for electronic image mirroring, in particular for vertical and horizontal image mirroring. In particular, the electronic camera can be a CCD camera, i.e. a camera with a CCD image sensor, or a CMOS camera, i.e. a camera with a CMOS image sensor.

The camera-adaptor combination according to the invention allows the implementation of the advantages of the camera adaptor according to the invention in conjunction with imaging the right way up and the right way round.

In the camera-adaptor combination, the electronic camera can additionally comprise a unit for the electronic displacement of the image in a perpendicular fashion with respect to the optical axis, in particular in two dimensions. In this case, the camera adaptor does not need to comprise an adjustment device for bringing about a relative movement between a mounted camera and the objective-lenses combination perpendicular to the optical axis.

In the camera-adaptor combination according to the invention, the camera can have, in particular, three image sensors and a color-splitting prism block. Cameras with three image sensors of the same size as in a camera with a single image sensor supply a higher resolution and are particularly suitable for recording moving color images. Moreover, there is no need for color interpolation, which is needed in the case of a camera with only one image sensor.

In a specific refinement of the camera-adaptor combination, the electronic camera has a ⅓-inch image sensor and the focal length of the objective-lenses combination in the camera adaptor lies in the region of between 45 mm and 55 mm, with the absolute value of the partial focal length of the lens or lens combination on the camera side being <80 mm, in particular <70 mm and more particularly <62 mm. As mentioned previously, the objective-lenses combination of the camera adaptor in such a refinement can be inserted completely or almost completely into the connecting piece of the decoupling element of an optical observation instrument, and so the overall installation length of a camera-adaptor combination arranged on the medical-optical observation system is very small. The same holds true for a further specific refinement of the camera-adaptor combination, in which the electronic camera has at least one ½-inch image sensor and in which the focal length of the objective-lenses combination in the camera adaptor lies in the region of between 55 mm and 75 mm, with the absolute value of the partial focal length of the lens or lens combination on the camera side being <110 mm, in particular <95 mm and more particularly <85 mm.

Further features, properties and advantages of the present invention emerge from the following description of exemplary embodiments with reference to the attached figures.

DETAILED DESCRIPTION OF THE PREFERRED EMBODIMENTS

Figure 1:
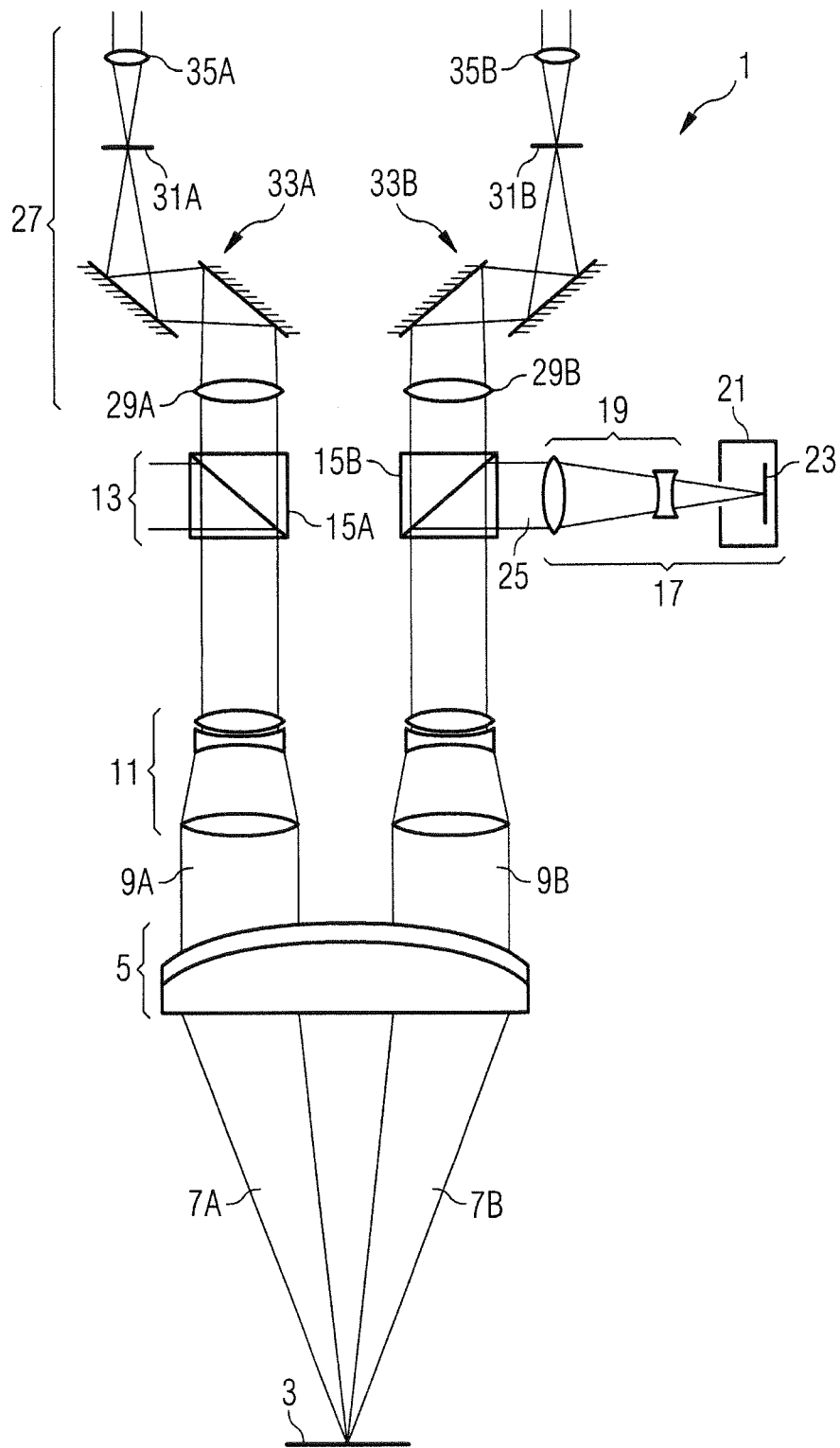
FIG. 1 shows a schematic illustration of a surgical microscope with a camera-adaptor combination arranged thereon.

The basic design of a surgical microscope with a camera-adaptor combination arranged thereon will be explained in the following text with reference to FIG. 1.

The surgical microscope 1 comprises, as an essential component, an objective 5 to face an observation object 3, which objective is illustrated in the present exemplary embodiment as a cemented component constructed from two partial lenses cemented together. The observation object 3 is arranged in the focal plane of the objective 5 and so a divergent bundle of rays emanating from the observation object 3 is imaged at infinity by the objective 5, that is to say the bundle of rays is converted into a parallel bundle of rays 9 after passing through the objective 5. Instead of a single objective lens, as is used in the present exemplary embodiment, it is however also possible to use an objective-lenses system made of a plurality of single lenses, such as a so-called varifocal lens system, by means of which the working distance of the microscope, i.e. the distance of the focal plane from the objective-lenses system, can be varied. In such a varifocal system, the observation object 3 arranged in the focal plane is also imaged at infinity and so there is also a parallel bundle of rays on the image side in the case of a varifocal lens system.

A magnification changer 11, which can be designed either, like in the exemplary embodiment, as a zoom system for a step-less change in the magnification factor or as a so-called Galilean system for a stepped change in the magnification factor, is arranged on the image side of the objective 5. In a zoom system, which can for example be constructed from a lens combination with three lenses, the two object-side lenses can be displaced in order to vary the magnification factor. By contrast, in a Galilean system, there are a plurality of fixed lens combinations, which can alternately be inserted into the beam path. Both the zoom system and a Galilean changer convert an object-side parallel bundle of rays into an image-side parallel bundle of rays with a different bundle diameter. The magnification changer is already part of the binocular beam path of the microscope, i.e. it has a separate lens combination for each stereoscopic partial bundle of rays 9A, 9B in the surgical microscope.

On the image side, the magnification changer 11 is adjoined by an interface 13 by means of which external instruments can be connected to the surgical microscope 1. In the present exemplary embodiment, the interface 13 is used to decouple the parallel stereoscopic partial bundles of rays 9A, 9B from the surgical microscope. In addition, it can also be used to couple a parallel bundle of rays into the surgical microscope 1, for example for the purpose of reflecting in data or other information. In the present exemplary embodiment, it comprises beam splitter prisms 15a, 15b, which are arranged in the respective stereoscopic partial beam paths and in which part of the respective partial bundle of rays 9A, 9B are deflected for decoupling.

The surgical microscope 1 illustrated in FIG. 1 has arranged on the interface 13 a camera-adaptor combination 17 which comprises a camera adaptor 19 and a camera 21 attached thereto with at least one electronic image sensor 23, e.g. with a CCD sensor or a CMOS sensor. The camera adaptor 19 converts the parallel bundle of rays 25, coupled out of the beam path of the microscope 1 by the beam splitter prism 15b, into a convergent bundle of rays and thus the observation object is imaged on the at least one electronic image sensor 23.

The camera 21 can be a photo camera, which records images of the observation object 3 for documentation purposes, or a video camera by means of which video images of the operation are generated for e.g. the operating staff, which images can then be displayed on a monitor or another visual instrument.

Although only one camera-adaptor combination, which focuses a partial bundle of rays 25 onto an electronic camera chip 23, is illustrated in the present exemplary embodiment, arranged on the interface 13 there can also be a further camera-adaptor combination, which focuses a parallel bundle of rays decoupled from the other partial beam path onto an electronic image sensor of a camera. It is then possible to record stereoscopic images or stereoscopic video images, which can be viewed using, for example, a head-mounted display.

On the image side, the interface 13 is adjoined by a binocular tube 27. The latter has two tube objectives 29a, 29b, which focus the respective parallel bundle of rays 9a, 9b onto an intermediate image plane 31, that is to say they image the observation object 3 on the respective intermediate image plane 31a, 31b. The intermediate images situated in the intermediate image planes 31a, 31b are ultimately imaged at infinity again by eyepiece lenses 35a, 35b and so an observer, for example a treating medical practitioner or an assistant, can observe the intermediate image with a relaxed eye. Moreover, a mirroring system or prisms 33a, 33b increases or increase the distance between the two partial bundles of rays 9a, 9b in the binocular tube in order to match that distance to the distance between the eyes of the observer.

Figure 2:
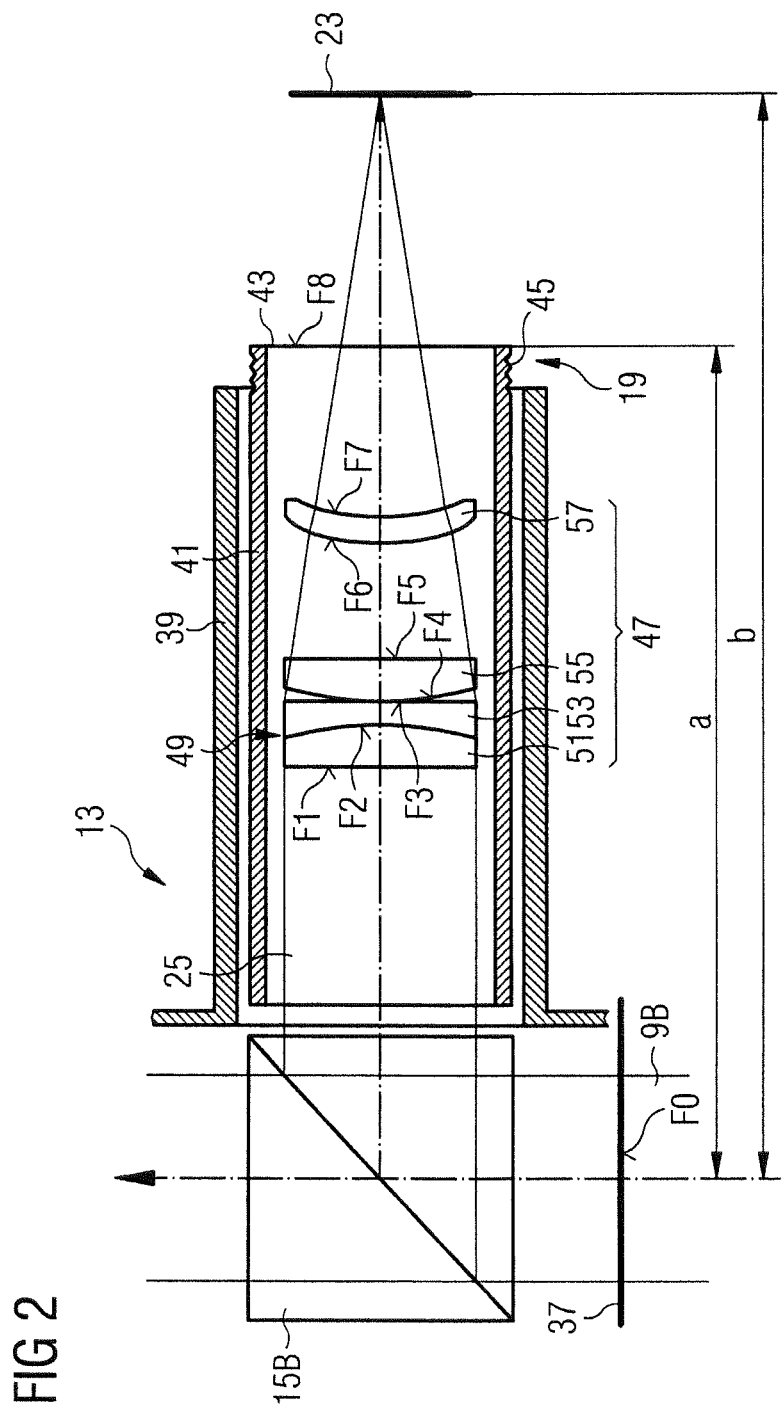
FIG. 2 shows a schematic illustration of a first exemplary embodiment of the camera adaptor.

A first exemplary embodiment of the camera adaptor 19 is described in the following text with reference to FIG. 2. In addition to the camera adaptor 19, the figure shows the electronic image sensor 23 and the beam splitter prism 15b, which is arranged in the partial bundle of rays 9b and by means of which the parallel bundle of rays 25 is coupled out of the parallel bundle of rays 9b. FIG. 2 furthermore schematically sketches the position of the entrance pupil 37, that is to say the position of the image, on the object side, of the opening defining the aperture of the camera adaptor 19. It should be noted that the position of the entrance pupil 37 is merely sketched schematically and this does not necessarily correspond to the precise position. The entrance pupil 37 is situated in the interior of the surgical microscope, between the beam splitter prism 15b and the objective 5.

In the present exemplary embodiment, the camera adaptor 19 comprises a push-on sleeve 41 as an instrument connector part for the connection to the interface 13, which sleeve can almost be completely inserted into a connecting piece 39 of the interface 13. Only the camera connector part 43 protrudes out of the connecting piece 39. In the present exemplary embodiment, the camera connector part is designed as a so-called C-mount 45, i.e. the camera adaptor 19 has a corresponding male thread. In principle, other systems for connecting a camera can be used instead of the C-mount, for example a CS mount or a bayonet cap.

Figure 8:
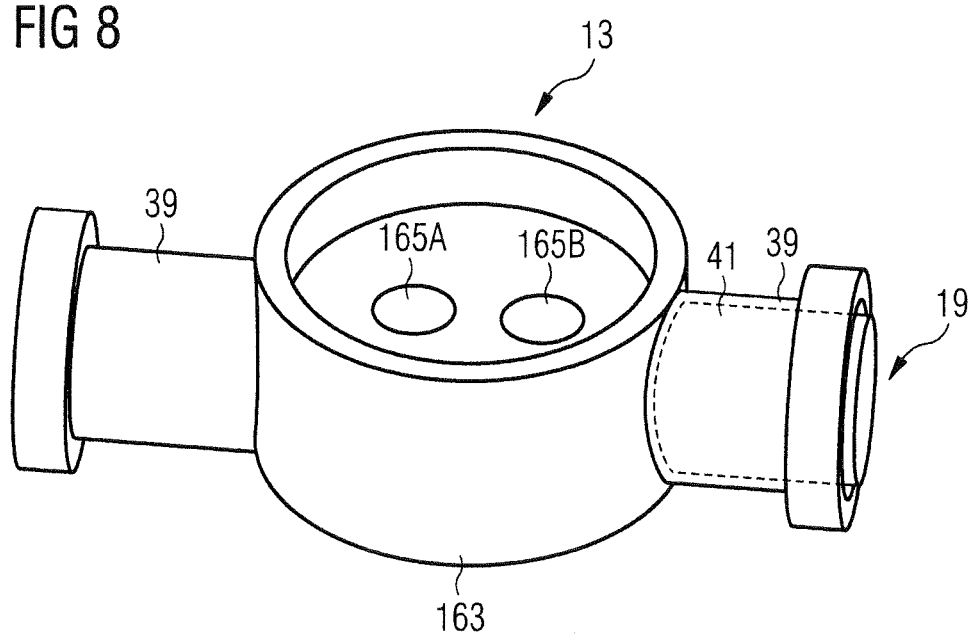
FIG. 8 shows a perspective illustration of an optical interface of a surgical microscope with a camera adaptor arranged thereon.

An interface 13 with two connecting pieces 39, in which the push-on sleeve 41 of a camera adaptor 19 is largely inserted into one of the connecting pieces 39, is illustrated in perspective in FIG. 8. In addition to the connecting piece 39, the base body 163 of the interface and openings 165a, 165b for the parallel partial bundles of rays 9a, 9b to pass through can be recognized. The beam splitter prisms 15A, 15B arranged in the interior of the base body 163 cannot be seen in this figure.

The camera adaptor 19 comprises an objective-lenses system 47, the total focal length 0 of which lies between 45 mm and 55 mm in the present exemplary embodiment. This objective-lenses system is designed as a tele-system and has a leading lens combination 49 on the instrument side containing, in the present exemplary embodiment, three single lenses 51, 53, 55. The two single lenses 51, 53 arranged at the instrument-side end of the lens combination 49 are cemented together to form a cemented component, which contributes to the color correction of the objective-lenses system 47.

On the camera side, the objective-lenses system 47 in the present exemplary embodiment comprises a final single lens 57, in which the partial focal length is negative and which is arranged at a distance from the lens combination 49 corresponding to a multiple of its thickness. The absolute value of the partial focal length of this camera-side lens 57 is less than 80 mm, in particular less than 70 mm and preferably less than 62 mm. An objective-lenses system 47 designed in this fashion constitutes a tele-objective, that is to say an objective whose focal length is greater than its installation length.

A specific example of an objective-lenses system with a total focal length of 50 mm and which is optimized for a ⅓-inch CCD chip is reproduced in Table 1. The individual optical surfaces, from the object side of the objective-lenses system to the image side of the objective-lenses system, are in this case referred to by F0, F1, etc. Here, the surface F0 constitutes the entrance pupil of the objective-lenses system 47 and the surface F8 constitutes the C-mount reference plane of the camera head. The negative partial focal length of the camera-side single lens is 61 mm.

TABLE 1

| Surface | Radius of curvature (mm) | Distance to the next surface (mm) | Glasses | Refractive index at 535 nm | half the free diameter (mm) |
|---|---|---|---|---|---|
| F0 | 0.00000 | 70.0000 | — | — | 6.000 |
| F1 | 45.91898 | 3.5500 | N-FK51A | 1.48836 | 6.000 |
| F2 | −19.83902 | 1.6170 | N-KZFS2 | 1.56158 | 6.000 |
| F3 | −390.70493 | 0.0500 | | 1.00000 | 6.000 |
| F4 | 18.49298 | 2.9160 | N-FK51A | 1.48836 | 6.000 |
| F5 | 88.25643 | 8.1777 | | 1.00000 | 6.000 |
| F6 | 12.89931 | 1.5810 | N-KZFS11 | 1.64243 | 6.000 |
| F7 | 9.25070 | 12.4950 | | 1.00000 | 5.500 |
| F8 | 0.00000 | — | | — | — |

In the case of an objective-lenses system 47 with the parameters as per Table 1, the diameter of the lenses and of the entrance pupil is preferably 12 mm and the distance of the first lens surface F1 to the C-mount reference plane of the camera head F8 is 30.4 mm. A very good imaging quality can be attained by the 4 lenses of the objective-lenses system 47 in this case with relatively few lenses—and thus with relatively low costs. Thus, in relation to the optical axis, a mean RMS wavefront aberration of <0.08 lambda (lambda=515.7 nm), in particular of <0.05 lambda and more particularly of <0.03 lambda can be obtained at wavelengths of 625 nm, 535 nm and 456 nm in the best focusing plane for all three wavelengths combined. This corresponds to a Strehl ratio of >0.8, in particular >0.9 and more particularly >0.95. A Strehl ratio of 1 would signify an aberration-free image. In actual fact, an objective-lenses system according to the parameters from Table 1 obtained a mean RMS wavefront aberration of 0.015 lambda, which corresponds to a Strehl ratio of 0.99, that is to say it lies in the vicinity of perfect imaging. Such an objective-lenses system moreover makes it possible to obtain a distance a of no more than 72 mm, in particular of no more than 66 mm and preferably of no more than 60 mm, between the optical axis of the beam path in the medical-optical observation instrument, to which the camera adaptor is coupled, and the C-mount reference plane of the camera head F8. Then, the distance b between the optical axis of the beam path in the medical-optical observation instrument, to which the camera adaptor is coupled, and the image plane 23 in air is no more than 83 mm, in particular no more than 77 mm and preferably no more than 71 mm.

The camera-adaptor arrangement illustrated in FIG. 2 illustrates an arrangement with a camera, which only has a single electronic image sensor 23. Since a CCD sensor or a CMOS sensor is fundamentally insensitive to color, so-called Bayer filters are arranged upstream of the sensors, in which filters every pixel of the sensor is associated with a red-color filter, a green-color filter or a blue-color filter. Thus, only a proportion of the pixels are available for each color and this reduces the resolution of the sensor. This holds true for both CCD sensors and CMOS sensors. Moreover, cameras with only one sensor require a color interpolation since each pixel only has information about one of the primary colors.

Figure 3:
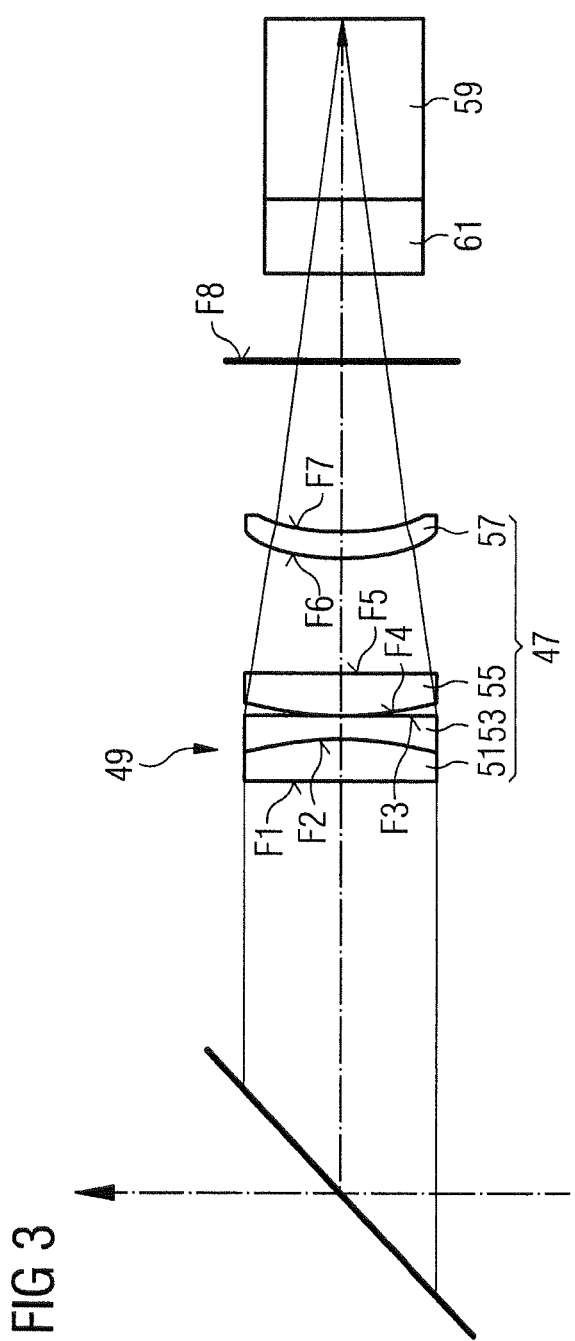
FIG. 3 shows the camera adaptor of the first exemplary embodiment in conjunction with a 3CCD camera.

However, it is also possible to use a camera with three electronic image sensors, for example a so-called 3CCD camera, as a camera 59 in the camera-adaptor combination 17 as an alternative to using a camera with a single electronic image sensor. The disadvantages in respect of resolution and color interpolation occurring in a single image sensor can thus be overcome. An exemplary embodiment of such a camera-adaptor combination with a 3CCD camera 59 is shown schematically in FIG. 3. The beam splitter, the connecting piece and the push-on sleeve have not been illustrated in the figure for reasons of clarity. However, these do not differ from those in FIG. 2. The discussion with reference to FIG. 2 relating to the optical data of the objective-lenses system 47 also analogously holds true for the exemplary embodiment illustrated in FIG. 3.

In contrast to the exemplary embodiment illustrated in FIG. 2, the camera comprises three CCD sensors, each of which is associated with one of the three primary colors (the three image sensors are not illustrated separately in the figure for reasons of clarity). The convergent bundle of rays incident on the camera 59 is split by means of a color-splitter prism block 61 into three different bundles of rays with the respective primary color, e.g. red, blue, green, and each of the three bundles of rays is supplied to a different one of the three CCD sensors.

A second exemplary embodiment of the camera-adaptor combination according to the invention will be described in the following text with reference to FIG. 4. In this exemplary embodiment too, the camera adaptor 119 has a push-on sleeve 141, which can almost be completely inserted into the connecting piece 39 of an interface 13 of the surgical microscope. As in the exemplary embodiment described with reference to FIG. 2, it is only the camera connector part 143 with the thread 145 of the C-mount connector that protrudes out of the push-on sleeve 141.

The camera adaptor 119 has an objective-lenses combination 147 tele-system, which comprises a leading lens combination 149 on the instrument side consisting of three lenses 151, 153, 155 and a final single lens 157 on the camera side with a negative focal length. The single lens 157 is arranged at a distance from the lens combination 149, which distance corresponds to a multiple of the thickness of said single lens. The two lenses 151, 153 of the instrument-side lens system 149 closest to the beam splitter of the interface are cemented to form a cemented component. In the present exemplary embodiment, the total focal length of the objective-lenses system 147 lies in the region of between 55 mm and 120 mm, and the focal length of the camera-side single lens 157 is, in absolute terms, <110 mm, in particular <95 mm and preferably <85 mm. The entrance pupil 137 of the objective-lenses system 147 is situated deep within the interior of the surgical microscope, between the beam splitter 15b and the main objective 5.

The objective-lenses combination 147 is particularly suitable for using a camera with a ½-inch image sensor 123, that is to say an image sensor with an image diagonal of 8 mm. A specific embodiment variant of the objective-lenses system with a total focal length of 66 mm and an absolute value of the negative focal length of the camera-side single lens 157 of 84 mm is reproduced in Table 2.

TABLE 2

| Surface | Radius of curvature (mm) | Distance to the next surface (mm) | Glasses | Refractive index at 535 nm | half the free diameter (mm) |
| --- | --- | --- | --- | --- | --- |
| G0 | 0.00000 | 70.0000 | — | — | 8.000 |
| G1 | 66.34024 | 3.4950 | N-FK51A | 1.48836 | 8.000 |
| G2 | −24.73168 | 1.5890 | N-KZFS2 | 1.56158 | 8.000 |
| G3 | −770.79316 | 0.0500 | | 1.00000 | 8.000 |
| G4 | 22.90312 | 2.5660 | N-FK51A | 1.48836 | 8.000 |
| G5 | 111.43200 | 7.8018 | | 1.00000 | 8.000 |
| G6 | 17.27856 | 3.3343 | N-KZFS11 | 1.64243 | 8.000 |
| G7 | 12.08697 | 26.4040 | | 1.00000 | 7.000 |
| G8 | 0.00000 | — | | — | — |

In the case of an objective-lenses system with the parameters as per Table 2, the diameter of the entrance pupil is preferably 16 mm and the distance between the first lens surface G1 and the C-mount reference plane of the camera head G8 is 45.2 mm. Using these parameters, an optical imaging quality on the optical axis with a mean RMS wavefront aberration of <0.8 lambda at lambda=515.7 nm (corresponds to a Strehl ratio of >0.8), in particular of <0.5 lambda (corresponds to a Strehl ratio of >0.9) and more particularly of <0.03 lambda (corresponds to a Strehl ratio of >0.95) can be obtained at the three wavelengths of 625 nm, 635 nm and 465 nm in the best focusing plane for all three wavelengths combined. Specifically, an RMS wavefront aberration of 0.012 lambda was obtained with the parameters specified in Table 2 and this corresponds to a Strehl ratio of 0.99.

Figure 4:
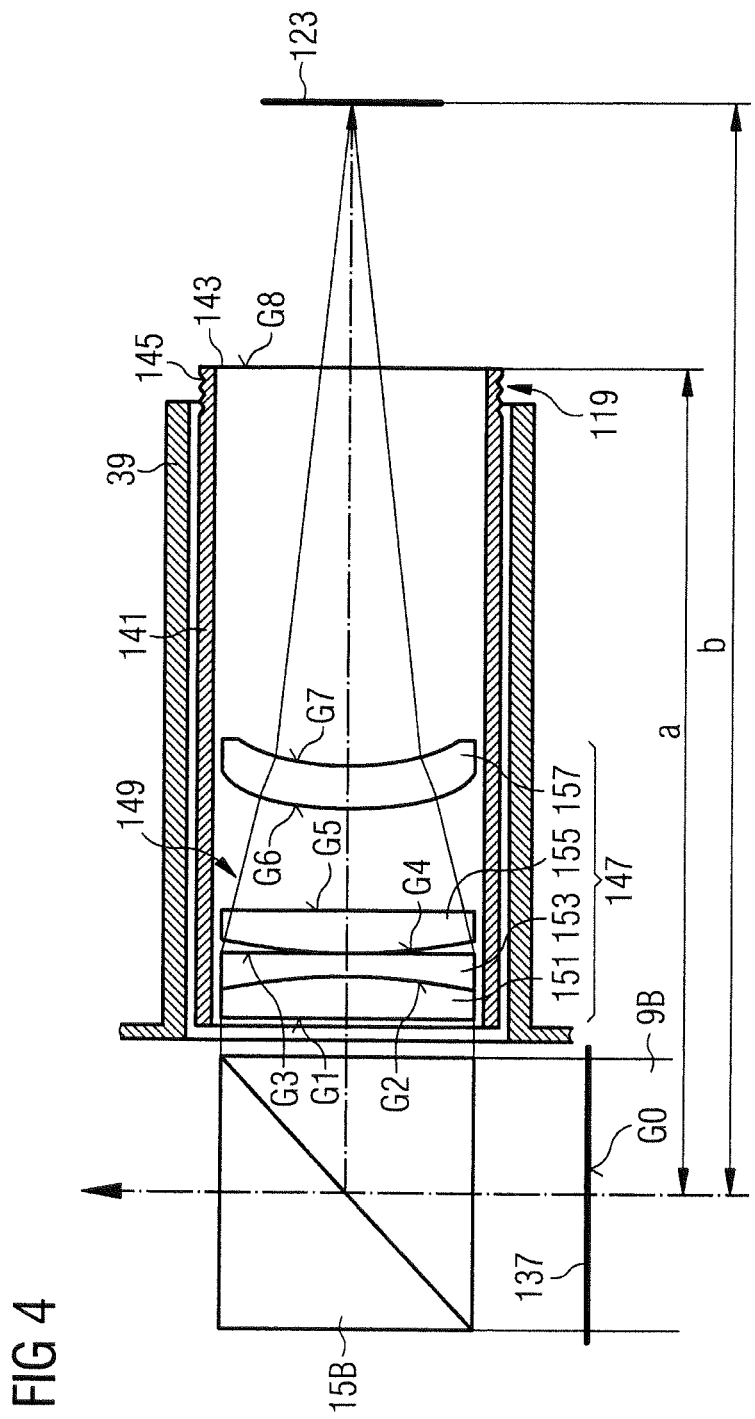
FIG. 4 shows a schematic illustration of a second exemplary embodiment of the camera adaptor.

Using the specified objective focal lengths of the second exemplary embodiment and the specified focal lengths of the camera-side single lens 157, a distance a of no more than 72 mm, in particular of no more than 66 mm and preferably of no more than 60 mm, can be implemented in the camera adaptor 119 illustrated in FIG. 4 between the optical axis of the beam path in the medical-optical observation instrument, to which the camera adaptor is coupled, and the C-mount reference plane of the camera head G8. If there is air between the C-mount reference plane of the camera head G8 and the image sensor 123, it is additionally possible to obtain a distance of no more than 83 mm, in particular of no more than 77 mm and preferably of no more than 71 mm, between the optical axis of the beam path in the medical-optical observation instrument, to which the camera adaptor is coupled, and the image sensor. This holds true in particular if a camera with only a single electronic image sensor 23 is used as a camera.

Figure 5:
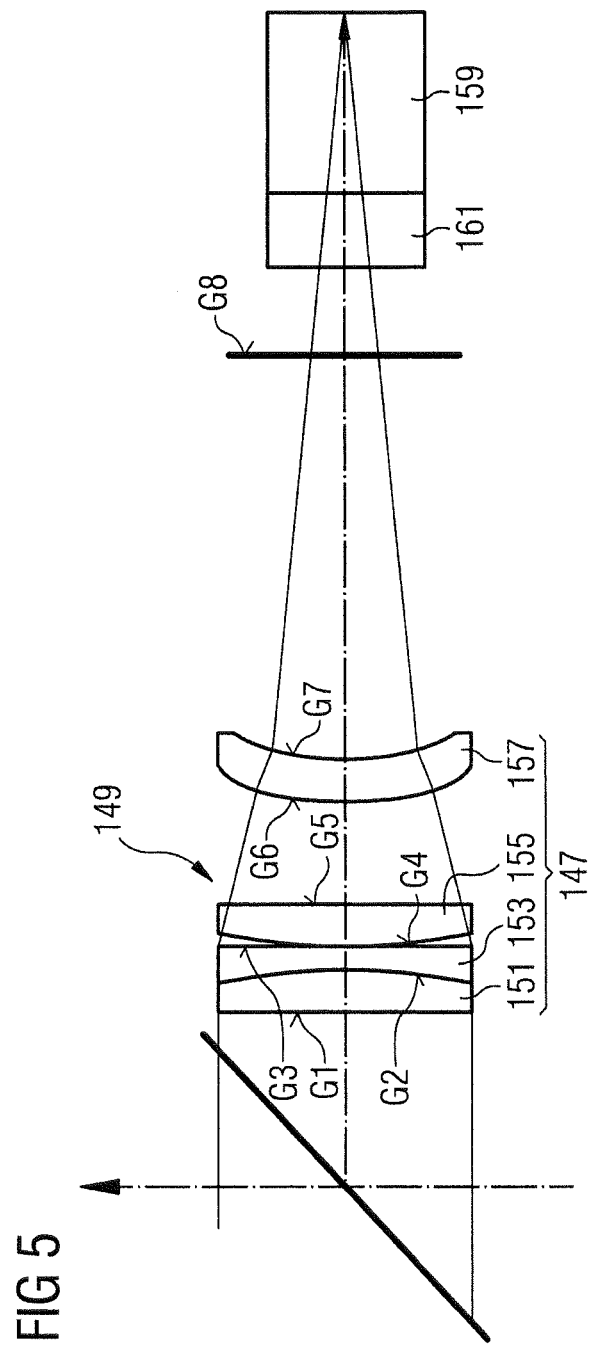
FIG. 5 shows the camera adaptor of the second exemplary embodiment in conjunction with a 3CCD camera.

As in the first exemplary embodiment, the camera adaptor 119 of the exemplary embodiment can also be combined with a camera having three separate image sensors. A corresponding camera-adaptor combination is illustrated in FIG. 5. Instead of the camera with a single electronic image sensor 123, the combination has a camera 159 with three electronic image sensors, in which the image sensors respectively have an image diagonal of 8 mm. In order to supply a converging partial bundle of rays of a single primary color to the image sensors in each case, the camera 159 comprises a color-splitter prism block 161 on the input side, which prism block splits the incident convergent bundle of rays into three bundles of rays, each with one primary color, and supplies the bundles of rays to the respective electronic image sensor. It is also possible to use both CCD sensors and CMOS sensors as electronic image sensors in the camera 159.

Figure 6:
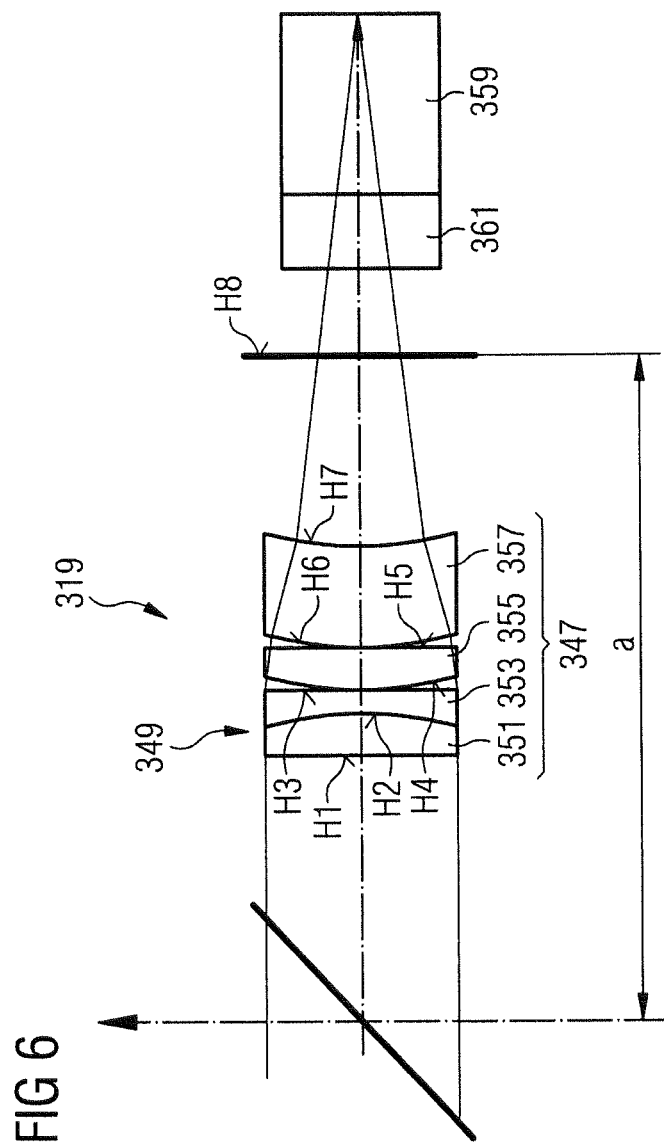
FIG. 6 shows a third exemplary embodiment of the camera adaptor in conjunction with a 3CCD camera.

A third exemplary embodiment of the camera-adaptor combination according to the invention will be described in the following text with reference to FIG. 6. The figure shows the camera adaptor combined with a camera 359, which has three separate image sensors and a beam-splitter prism 361. In this exemplary embodiment too, the camera adaptor has a push-on sleeve (not illustrated in FIG. 6) which can almost be completely inserted into the connecting part of an interface of the surgical microscope. As in the exemplary embodiment described in relation to FIG. 2, it is only the camera connector part with the thread of the C-mount connector that protrudes out of the push-on sleeve.

The camera adaptor 319 of the third exemplary embodiment has an objective-lenses combination 347 in the form of a compact tele-system, which comprises a leading lens combination 349 on the instrument side consisting of three lenses 351, 353, 355 and a final single lens 357 on the camera side with a negative focal length, in which the single lens 357 is arranged so closely to the lens combination 349 that it touches the latter. The two lenses 351, 353 of the instrument-side lens system 349 closest to the beam splitter of the interface are cemented to form a cemented component. In the present exemplary embodiment, the total focal length of the objective-lenses system 347 lies in the region of between 40 mm and 80 mm, and the focal length of the camera-side single lens 357 is, in absolute terms, less than 80 mm, in particular less than 70 mm and preferably less than 65 mm. The entrance pupil of the objective-lenses system 347 is situated deep within the interior of the surgical microscope, between the beam splitter 15b and the main objective 5.

The objective-lenses combination 347 is particularly suitable for using a camera with a ½-inch image sensor 323, that is to say an image sensor with an image diagonal of 6 mm. A specific embodiment variant of the objective-lenses system with a total focal length of 50 mm and an absolute value of the negative focal length of the camera-side single lens 357 of 62 mm is reproduced in Table 3.

TABLE 3

| Surface | Radius of curvature (mm) | Distance to the next surface (mm) | Glasses | Refractive index at 535 nm | half the free diameter (mm) |
|---|---|---|---|---|---|
| H0 | 0.00000 | 70.0000 | — | — | 6.000 |
| H1 | 57.9391 | 3.6400 | N-FK51A | 1.48836 | 6.000 |
| H2 | −16.39986 | 1.6170 | N-KZFS2 | 1.56158 | 6.000 |
| H3 | 979.98046 | 0.0500 | | 1.00000 | 6.000 |
| H4 | 20.78510 | 2.9500 | N-FK51A | 1.48836 | 6.000 |
| H5 | −362.81471 | 0.1500 | | 1.00000 | 6.000 |
| H6 | 16.95535 | 7.0000 | N-KZFS2 | 1.56158 | 6.000 |
| H7 | 9.71965 | 15.2954 | | 1.00000 | 5.500 |
| H8 | 0.00000 | — | — | — | — |

In the case of an objective-lenses system with the parameters as per Table 3, the diameter of the entrance pupil is preferably 12 mm and the distance between the first lens surface H1 and the C-mount reference plane of the camera head H8 is 30.7 mm. Using these parameters, an optical imaging quality on the optical axis with a mean RMS wavefront aberration of <0.8 lambda at lambda=515.7 nm (corresponds to a Strehl ratio of >0.8), in particular of <0.5 lambda (corresponds to a Strehl ratio of >0.9) and more particularly of <0.03 lambda (corresponds to a Strehl ratio of >0.95) can be obtained at the three wavelengths of 625 nm, 635 nm and 465 nm in the best focusing plane for all three wavelengths combined. Specifically, an RMS wavefront aberration of 0.019 lambda was obtained with the parameters specified in Table 3 and this corresponds to a Strehl ratio of 0.98.

Such an objective-lenses system makes it possible to obtain a distance a of no more than 72 mm, in particular of no more than 66 mm and preferably of no more than 60 mm between the optical axis of the beam path in the medical-optical observation instrument, to which the camera adaptor is coupled, and the C-mount reference plane of the camera head H8. Then, the distance between the optical axis of the beam path in the medical-optical observation instrument, to which the camera adaptor is coupled, and the image plane in air is no more than 83 mm, in particular no more than 77 mm and preferably no more than 71 mm.

It should be noted here that, in the exemplary embodiments described with reference to FIGS. 2 to 6, the cemented component of the instrument-side lens systems is in each case formed by the two leading lenses. However, it is also possible to design the lens systems with a single lens as leading lens and to form the cemented component by cementing the subsequent lenses, so that the order of single lens and cemented component is interchanged compared to the instrument-side lens combinations illustrated in FIGS. 2 to 6.

Figure 7:
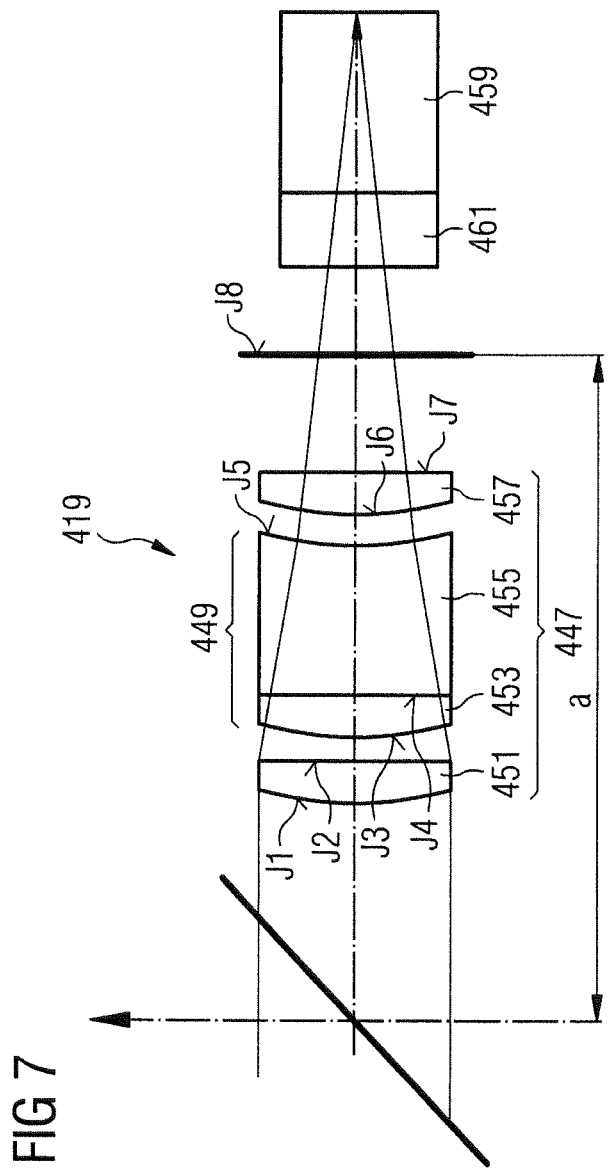
FIG. 7 shows a fourth exemplary embodiment of the camera adaptor in conjunction with a 3CCD camera.

A fourth exemplary embodiment of the camera-adaptor combination according to the invention will be described in the following text with reference to FIG. 7. The figure shows the camera adaptor combined with a camera 459, which has three separate image sensors and a beam splitter prism 461. In this exemplary embodiment too, the camera adaptor has a push-on sleeve (not illustrated in FIG. 7) which can almost be completely inserted into the connecting part of an interface of the surgical microscope. As in the exemplary embodiment described in relation to FIG. 2, it is merely the camera connector part with the thread of the C-mount connector that protrudes out of the push-on sleeve.

The camera adaptor 419 of the fourth exemplary embodiment has an objective-lenses combination 447 in the form of a triplet, which comprises a leading single lens 451 with positive refractive power on the instrument side, a final single lens 457 with positive refractive power on the camera side and, arranged therebetween, a lens combination 449 of two lenses 453, 455 cemented together to form a cemented component. The lens combination 449 has negative refractive power. In the present exemplary embodiment, the total focal length of the objective-lenses system 447 is in the region of between 40 mm and 80 mm. The entrance pupil of the objective-lenses system 447 is situated deep within the interior of the surgical microscope, between the beam splitter 15b and the main objective 5.

The objective-lenses combination 447 is particularly suitable for using a camera with a ½-inch image sensor, that is to say an image sensor with an image diagonal of 6 mm. A specific embodiment variant of the objective-lenses system 447 with a total focal length of 50 mm is reproduced in Table 4.

TABLE 4

| Surface | Radius of curvature (mm) | Distance to the next surface (mm) | Glasses | Refractive index at 535 nm | half the free diameter (mm) |
|---|---|---|---|---|---|
| J0 | 0.00000 | 70.0000 | — | — | 6.000 |
| J1 | 61.01557 | 2.7816 | N-FK51A | 1.48836 | 6.000 |
| J2 | −152.02793 | 1.6238 | | 1.00000 | 6.000 |
| J3 | 17.33755 | 3.9500 | N-FK51A | 1.48836 | 6.000 |
| J4 | −46.48729 | 10.9476 | N-KZFS2 | 1.56158 | 6.000 |
| J5 | 12.02361 | 2.1051 | | 1.00000 | 6.000 |
| J6 | 19.15615 | 3.3469 | N-FK51A | 1.48836 | 6.000 |
| J7 | 69.92257 | 9.1185 | | 1.00000 | 6.000 |
| J8 | 0.00000 | — | — | — | — |

In the case of an objective-lenses system with the parameters as per Table 4, the diameter of the entrance pupil is preferably 12 mm and the distance between the first lens surface H1 and the C-mount reference plane of the camera head H8 is 33.9 mm. Using these parameters, an optical imaging quality on the optical axis with a mean RMS wavefront aberration of <0.8 lambda at lambda=515.7 nm (corresponds to a Strehl ratio of >0.8), in particular of <0.5 lambda (corresponds to a Strehl ratio of >0.9) and more particularly of <0.03 lambda (corresponds to a Strehl ratio of >0.95) can be obtained at the three wavelengths of 625 nm, 635 nm and 465 nm in the best focusing plane for all three wavelengths combined. Specifically, an RMS wavefront aberration of 0.021 lambda was obtained with the parameters specified in Table 4 and this corresponds to a Strehl ratio of 0.98.

Such an objective-lenses system makes it possible to obtain a distance a of no more than 72 mm, in particular of no more than 66 mm and preferably of no more than 60 mm between the optical axis of the beam path in the medical-optical observation instrument, to which the camera adaptor is coupled, and the C-mount reference plane of the camera head H8. Then, the distance between the optical axis of the beam path in the medical-optical observation instrument, to which the camera adaptor is coupled, and the image plane in air is no more than 83 mm, in particular no more than 77 mm and preferably no more than 71 mm.

Figure 9:
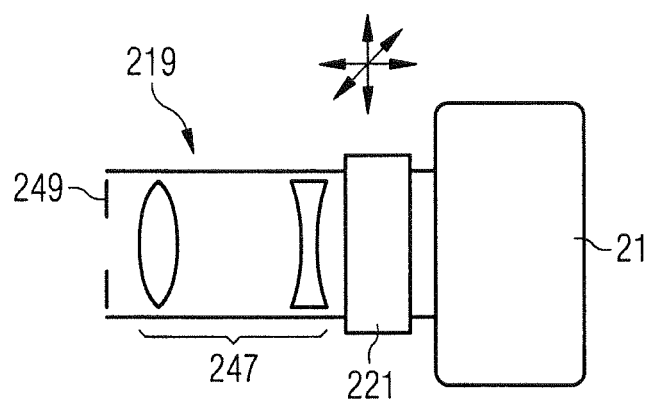
FIG. 9 shows a schematic illustration of a further exemplary embodiment of the camera adaptor according to the invention.

In principle, the camera-adaptor combination described in the exemplary embodiments can be marketed as a unit, i.e. the camera and objective are precisely matched to one another and adjusted, so that the user need not adjust them. However, in principle, it is also possible to market the camera and adaptor separately, such that adjustment by the user becomes necessary. The camera adaptor can have an adjustment apparatus for this purpose, by means of which the camera can be adjusted relative to the objective-lenses system. An exemplary embodiment of such a camera adaptor with a camera attached thereto is shown in FIG. 9. The camera adaptor 219, the camera 21 arranged thereon and, schematically, the objective-lenses system 247 of the camera adaptor 219 can be recognized. There is an adjustment unit 221 on the camera-side connector part of the camera adaptor 219, by means of which unit a relative displacement between the camera 21 and the objective-lenses system 247 can be implemented in three dimensions and, optionally, a tipping of the camera 21 relative to the optical axis. This makes an adjustment of the camera and camera adaptor possible.

The camera adaptor 219 can moreover have a variable stop 249, which, for example, can be designed as an iris stop. The stop 249 can set the illumination of the image sensor in the camera 21 and the depth of focus of the image.

However, even if the camera 21 and the camera adaptor 219 are marketed as a unit, i.e. as a camera-adaptor combination, it can be expedient to provide such an adjustment unit 221. By way of example, such an adjustment unit, which allows an adjustment perpendicular to the optical axis, can set the image position on the image sensor of the camera. A relative movement between the objective-lenses system 247 and the camera 21 along the optical axis moreover allows the focusing to be set.

As can be gathered from the described exemplary embodiments, the camera adaptor according to the invention merely has one linear optical axis, i.e. there is neither a mirror nor a prism for deflecting the beam path. Thus, the image is not erected in the camera adaptor for displaying the observation object 3 the right way up or the right way round. Therefore, the image erection for displaying the observation object 3 the right way up and the right way round is brought about electronically in the camera 21 in the camera-adaptor combination according to the invention.

Figure 10:
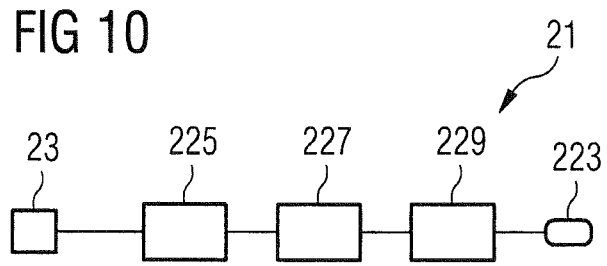
FIG. 10 shows a block diagram of a first exemplary embodiment of a camera used in the camera-adaptor combination according to the invention.

A block diagram of the camera 21 is illustrated in FIG. 10. The electronic image sensor 23 and an output interface 223 of the camera 21 for outputting the recorded images on a monitor, an electronic eyepiece, a head-mounted display, etc. are output. The camera 21 has a readout unit 225, which reads the electronic image sensor 23 and generates an electronic image. An electronic image-mirroring unit 227 is connected to the readout unit 225 for receiving the electronic images. The images received by the electronic image-mirroring unit 227 are then mirrored electronically in this unit in order to obtain a display of the observation object 3 that is the right way up and the right way round.

The camera 21 illustrated in FIG. 10 furthermore comprises an optional electronic image-displacement unit 229, which is connected to the electronic image-mirroring unit 227 for receiving the electronically mirrored images. The electronic image-displacement unit 229 can bring about a displacement of the electronic image perpendicular to the optical axis of the objective-lenses system in the camera adaptor. If there is no need to focus the image, the mechanical adjustment unit 221 can be dispensed with if there is an electronic image-displacement unit 229. The optional electronic image-displacement unit 229 outputs the possibly displaced electronic image via the output interface 223.

Figure 11:
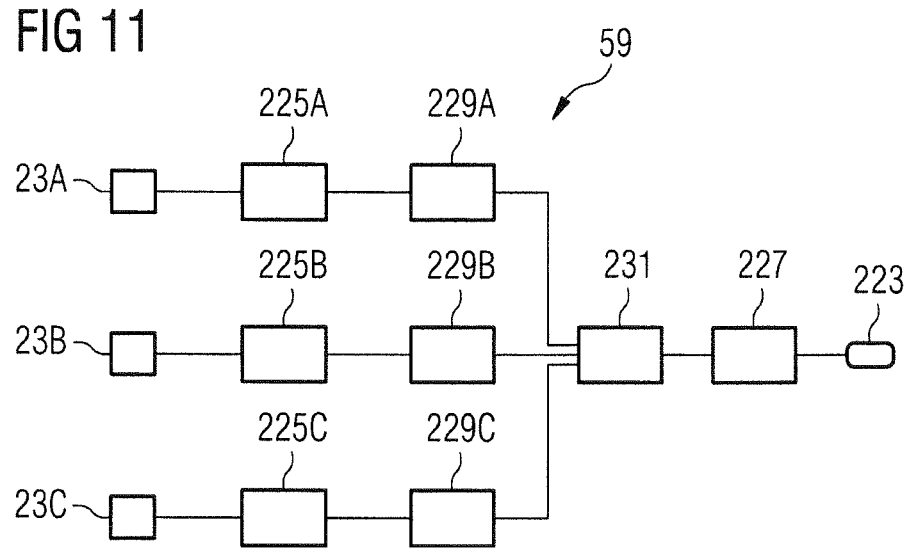
FIG. 11 shows a block diagram of a second exemplary embodiment of a camera used in the camera-adaptor combination.

It should be noted that the camera 21 illustrated schematically in FIG. 10 merely has one electronic image sensor 23. However, it is understood that the camera can also have three electronic image sensors, respectively one for each primary color. Such a camera 59 is illustrated schematically in FIG. 11 as a block diagram. It comprises three readout units 225a, 225b, 225c which are respectively assigned to one of the image sensors 23a, 23b, 23c for reading the corresponding image sensor 23a, 23b, 23c. The camera 59 in FIG. 11 furthermore comprises three optional electronic image-displacement units 229a, 229b, 229c. Each of these electronic image-displacement units is connected to one of the readout units 225a, 225b, 225c for receiving the corresponding electronic image (respectively in one of the three primary colors). Using the three electronic image-displacement units 229a, 229b, 229c, the individual partial images in the respective primary colors can be displaced not only perpendicular to the optical axis of the objective-lenses system 247, but also relative to one another. This makes it possible to compensate different image positions on the individual sensors 23a, 23b, 23c.

A combination unit 231, which is connected to the readout units for receiving the images or—as in the illustrated exemplary embodiment—to the optional electronic image-displacement units 229a, 229b, 229c for receiving the displaced images, combines the images to form a color image. The color images are then transmitted to an electronic image-mirroring unit 227, which is connected to the combination unit 231 and in which the color image is erected in order to obtain an illustration of the observation object 3 that is the right way up and the right way round. Finally, the erected image is output via the output interface 223. It should be noted here that the electronic image mirroring can also be brought about before combining the three primary color images to form a color image. In said case, three image-mirroring units, which would each be associated with one of the three image sensors, would be arranged upstream of the combination unit 231.

The described camera adaptor according to the invention allows for the provision of a cost-effective adaptor, the optical system of which satisfies the "Full HD Ready" requirements, but which, nevertheless, can be produced cost-effectively. As a result of the combination with a camera that makes electronic image-mirroring possible, it is possible to dispense with a reflective element in the camera adaptor, as a result of which an extremely short installation length of the camera adaptor can be implemented in conjunction with an objective-lenses combination designed as a tele-objective. The camera-adaptor combination according to the invention therefore can be used, for example, in a surgical microscope without impeding the treating medical practitioner.

The number of lenses of the camera adaptors described in the exemplary embodiments should not be understood strictly as the subject matter but should be understood functionally. The function carried out by a single lens in an objective-lenses combination can, in principle, also be implemented if the corresponding single lens is replaced by a lens combination having a plurality of lenses, which together lead to the same optical properties as in the single lens. In principle, this also holds true for replacing a lens in a lens combination by a plurality of lenses such that the number of lenses in the lens combination increases.

What is claimed is:

1. A camera adaptor (19, 119, 219, 319, 419) for connecting a camera (21, 59, 159, 359, 459) to an interface (13) of a medical-optical observation instrument (1) comprising a parallel beam path, in which the interface (13) is situated in the parallel beam path (9a, 9b) of the medical-optical observation instrument (1) and in which
the camera adaptor (19, 119, 219, 319, 419) has an instrument connector part (41, 141) for the connection to the interface of the medical-optical observation instrument and a camera connector part (43, 143) for the connection to a camera (21, 59, 159),
the beam path (43, 143) runs through the camera adaptor (19, 119, 219, 319, 419) along a linear optical axis, the camera adaptor (19, 119, 219, 319, 419) comprises an objective-lenses combination (47, 147, 247, 347, 447) with a total focal length in the region of between 40 mm and 120 mm, and the objective-lenses combination (47, 147, 247, 347, 447) has a lens combinations (49, 149, 349) of three lenses leading on the instrument side and which together have a positive partial focal length, the lens combination of three lenses (49, 149, 349) being followed, on a side toward the camera, by a single lens (57, 157, 357) with a negative partial focal length and the objective-lenses combination forms a tele-system (47, 147, 247, 347).

2. The camera adaptor (19, 119, 219, 319) of claim 1, in which the leading lens combination (49, 149, 349) on the instrument side comprises two lenses (51, 53, 151, 153, 351, 353) cemented together to form a cemented component.

3. The camera adaptor (19, 119, 219, 319) of claim 2, in which the lens surfaces (F1-F5, G1-G5, H1-H5) of the leading lens combination (49, 149, 349) on the instrument side have, as seen from the instrument side to the camera side, a positive or negative radius of curvature, a negative radius of curvature, a positive or negative radius of curvature, a positive radius of curvature and a positive or negative radius of curvature and the lens surfaces (F6, F7, G6, G7, H6, H7) of the final lens (57, 157, 357) on the camera side have, as seen from the instrument side to the camera side, a positive radius of curvature and a positive radius of curvature.

4. The camera adaptor (119) of claim 1, in which the absolute value of the partial focal length of the final lens or lens combination (157) on the camera side is less than 110 mm.

5. The camera adaptor (19) of claim 4, in which the total focal length of the objective-lenses combination (47) lies in the region of between 40 mm and 80 mm and the absolute value of the partial focal length of the final lens or lens combination (57) on the camera side is less than 80 mm.

6. The camera adaptor (19) of claim 4, in which the total focal length of the objective-lenses combination (47) lies in the region of between 55 mm and 120 mm and the absolute value of the partial focal length of the final lens or lens combination (157) on the camera side is less than 110 mm.

7. The camera adaptor (19, 119, 219, 319) of claim 1, in which the diameter of the entrance pupil is less than 18 mm.

8. The camera adaptor (219) of claim 1, which comprises an adjustment device (221), with the aid of which a relative movement between a mounted camera (21) and the objective-lenses combination (247) perpendicular to the optical axis can be brought about.

9. The camera adaptor (219) of claim 1, which comprises an adjustment device (221), with the aid of which a relative movement between a mounted camera (21) and the objective-lenses combination (247) along the optical axis can be brought about.

10. The camera adaptor (219) of claim 1, which has a tilting mechanism (221), with the aid of which a relative tilt between a mounted camera (21) and the objective-lenses combination (247) can be brought about.

11. The camera adaptor (219) of claim 1, in which there is a variable stop (249) in front of the objective-lenses combination (247) on the instrument side.

12. A camera-adaptor combination (17) for a medical-optical observation instrument (1) with the camera adaptor (19, 119, 219, 319) of claim 1 and an electronic camera (21, 59, 359) arranged on the camera connector part (43, 143) and comprising a unit for electronic image mirroring (227).

13. The camera-adaptor combination (17) of claim 12, in which the electronic camera (21, 59) comprises a unit for the electronic displacement (229) of the image in a perpendicular fashion with respect to the optical axis.

14. The camera-adaptor combination (17) of claim 12, in which the camera (59, 159, 359, 459) has three image sensors (23A, 23B, 23C) and a color-splitting prism block (61, 161, 361, 461).

15. The camera-adaptor combination (17) of claim 12, in which the electronic camera (21, 59) has at least one ⅓-inch image sensor (23), the focal length of the objective-lenses combination (47) in the camera adaptor (19) lies in the region of between 40 mm and 80 mm and the absolute value of the partial focal length of the lens or lens combination (57) on the camera side is less than 80 mm.

16. The camera-adaptor combination (17) of claim 12, in which the electronic camera (21, 159) has at least one ½-inch image sensor (23), the focal length of the objective-lenses combination (147) in the camera adaptor (19) lies in the region of between 55 mm and 120 mm and the absolute value of the partial focal length of the lens or lens combination (157) on the camera side is less than 110 mm.

17. A camera adaptor (419) for connecting a camera (459) to an interface (13) of a medical-optical observation instrument (1) comprising a parallel beam path, in which the interface (13) is situated in the parallel beam path (9a, 9b) of the medical-optical observation instrument (1) and in which the camera adaptor (419) has an instrument connector part (41, 141) for connection to the interface of the medical-optical observation instrument and a camera connector part (43, 143) for the connection to a camera (21, 59, 159), the beam path (43, 143) runs through the camera adaptor (419) along a linear optical axis, the camera adaptor (419) comprises an objective-lenses combination (447) with a total focal length in the region of between 40 mm and 120 mm, and the objective-lenses combination (447) has a single lens (451) leading on the instrument side and having a positive partial focal length, the single lens (451) leading on the instrument side being followed on a side toward the camera by a lens combination (449) with a negative partial focal length and having two lenses (453, 455), and the lens combination (449) with the negative partial focal length being followed on the side toward the camera by a single lens (457) with a positive partial focal length so that the objective-lenses combination forms a triplet (447).

18. The camera adaptor (419) of claim 17, in which the lens or lens combinations (449) with the negative partial focal length is/are a cemented component with the two lenses (453, 455) cemented together.

19. The camera adaptor (419) of claim 17, in which the lens surfaces (J1, J2) of the leading single lens (451) on the instrument side have, as seen from the instrument side to the camera side, a positive or negative radius of curvature and a positive or negative radius of curvature, the lens surfaces (J3-J5) of the cemented component (449) have, as seen from the instrument side to the camera side, a positive radius of curvature, a negative radius of curvature and a positive radius of curvature and the lens surfaces (J6, J7) of the final single lens (457) on the camera side have, as seen from the instrument side to the camera side, a positive radius of curvature and a positive or negative radius of curvature.

20. The camera adaptor (419) of claim 17, in which the objective-lenses combination (447) has four lenses (51, 53, 55, 57, 151, 153, 155, 157, 351, 353, 355, 357, 451, 453, 455, 457).

21. The camera adaptor (419) of claim 17, in which the diameter of the entrance pupil is less than 18 mm.

22. The camera adaptor (219) of claim 17, which comprises an adjustment device (221), with the aid of which a relative movement between a mounted camera (21) and the objective-lenses combination (247) perpendicular to the optical axis can be brought about.

23. The camera adaptor (219) of claim 17, which comprises an adjustment device (221), with the aid of which a relative movement between a mounted camera (21) and the objective-lenses combination (247) along the optical axis can be brought about.

24. The camera adaptor (219) of claim 17, which has a tilting mechanism (221), with the aid of which a relative tilt between a mounted camera (21) and the objective-lenses combination (247) can be brought about.

25. The camera adaptor (219) of claim 17, in which there is a variable stop (249) in front of the objective-lenses combination (247) on the instrument side.

26. A camera-adaptor combination (17) for a medical-optical observation instrument (1) with the camera adaptor (419) of claim 17 and an electronic camera (459) arranged on the camera connector part (43, 143) and comprising a unit for electronic image mirroring (227).

27. The camera-adaptor combination (17) of claim 26, in which the electronic camera (21, 59) comprises a unit for the electronic displacement (229) of the image in a perpendicular fashion with respect to the optical axis.

28. The camera-adaptor combination (17) of claim 26, in which the camera (59, 159, 359, 459) has three image sensors (23A, 23B, 23C) and a color-splitting prism block (461).

29. The camera-adaptor combination (17) of claim 26, in which the electronic camera (21, 59) has at least one ⅓-inch image sensor (23), the focal length of the objective-lenses combination (47) in the camera adaptor (19) lies in the region of between 40 mm and 80 mm and the absolute value of the partial focal length of the lens or lens combination (57) on the camera side is less than 80 mm.

30. The camera-adaptor combination (17) of claim 26, in which the electronic camera (21, 159) has at least one ½-inch image sensor (23), the focal length of the objective-lenses combination (147) in the camera adaptor (19) lies in the region of between 55 mm and 120 mm and the absolute value of the partial focal length of the lens or lens combination (157) on the camera side is less than 110 mm.

31. A camera adaptor (19, 119, 219, 319, 419) for connecting a camera (21, 59, 159, 359, 459) to an interface (13) of a medical-optical observation instrument (1) comprising a parallel beam path, in which the interface (13) is situated in the parallel beam path (9a, 9b) of the medical-optical observation instrument (1) and in which the camera adaptor (19, 119, 219, 319, 419) has an instrument connector part (41, 141) for the connection to the interface of the medical-optical observation instrument and a camera connector part (43, 143) for the connection to a camera (21, 59, 159), the beam path (43, 143) runs through the camera adaptor (19, 119, 219, 319, 419) along a linear optical axis, the camera adaptor (19, 119, 219, 319, 419) comprises an objective-lenses combination (47, 147, 247, 347, 447) with a total focal length in the region of between 40 mm and 120 mm, and the objective-lenses combination (47, 147, 247, 347, 447) consists of four lenses and there is, leading on the instrument side, a lens (451) or lens combination (49, 149, 349) with a positive partial focal length, which is followed, on the side toward the camera, by a lens (57, 157, 357) or lens combination (449) with a negative partial focal length.

32. The camera-adaptor combination (17) for a medical-optical observation instrument (1) with the camera adaptor (19, 119, 219, 319, 419) of claim 31 and an electronic camera (21, 59, 359, 459) arranged on the camera connector part (43, 143) and comprising a unit for electronic image mirroring (227).

* * * * *